United States Patent
Bi et al.

(10) Patent No.: US 8,374,675 B2
(45) Date of Patent: Feb. 12, 2013

(54) MAGNETIC RESONANCE ANGIOGRAPHY WITH FLOW-COMPENSATED AND FLOW-SENSITIVE IMAGING

(75) Inventors: Xiaoming Bi, Aurora, IL (US); Michaela Schmidt, Uttenreuth (DE); Peter Schmitt, Weisendorf (DE); Peter Weale, Chicago, IL (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 190 days.

(21) Appl. No.: 12/683,620

(22) Filed: Jan. 7, 2010

(65) Prior Publication Data

US 2010/0280357 A1    Nov. 4, 2010

(30) Foreign Application Priority Data

Apr. 30, 2009 (DE) .......................... 10 2009 019 596

(51) Int. Cl.
*A61B 5/055* (2006.01)
(52) U.S. Cl. .......................... 600/413; 600/419; 600/508
(58) Field of Classification Search .................. 600/410, 600/413, 419, 508, 509; 324/306, 307, 309
See application file for complete search history.

(56) References Cited

U.S. PATENT DOCUMENTS

| | | | |
|---|---|---|---|
| 5,031,624 A * | 7/1991 | Mistretta et al. | 600/419 |
| 5,329,925 A * | 7/1994 | NessAiver | 600/413 |
| 7,317,940 B2 | 1/2008 | Assmann | |
| 7,894,875 B2 | 2/2011 | Van Zijl et al. | |

FOREIGN PATENT DOCUMENTS

EP    1 060 708 A2    12/2000

OTHER PUBLICATIONS

"Non-Contrast-Enhanced MR Angiography Using 3D ECG-Synchronized Half-Fourier Fast Spin Echo," Miyazaki et al., J. of Magnetic Resonance Imaging, vol. 12 (2000) pp. 776-783.
"Peripheral MR Angiography: Separation of Arteries from Veins with Flow-Spoiled Gradient Pulses in Electrocardiography-Triggered Three-Dimensional Half-Fourier Fast Spin-Echo Imaging," Miyazaki et al., Radiology, vol. 227, No. 3 (2003) pp. 890-896.
"Flow Compensation in Balanced SSFP Sequences," Bieri et al., Magnetic Resonance in Medicine, vol. 54 (2005) pp. 901-907.
"Gradient Moment Nulling in Fast Spin Echo," Hinks et al., Magnetic Resonance in Medicine, vol. 32 (1994) pp. 698-706.

(Continued)

*Primary Examiner* — Ruth S Smith
(74) *Attorney, Agent, or Firm* — Schiff Hardin LLP (57) ABSTRACT

In a magnetic resonance angiography method with flow-compensated and flow-sensitive imaging and a magnetic resonance apparatus for implementing such a method, a first MR data set of the examination region is acquired with an imaging sequence in which vessels in the examination region are shown with high signal intensity, a second MR data set of the examination region with an imaging sequence in which the vessels in the examination region are shown with low signal intensity, and the angiographic magnetic resonance image is calculated in a processor by taking the difference of the first and second data set. The first data set is acquired with an imaging sequence with reduced flow sensitivity and the second data set is acquired with an imaging sequence with an increased flow sensitivity compared to the initial imaging sequence.

14 Claims, 6 Drawing Sheets

OTHER PUBLICATIONS

"Diffusion-Prepared Segmented Steady-State Free Precession: Application to 3D Black-Blood Cardiovascular Magnetic Resonance of the Thoracic Aorta and Carotid Artery Walls," Koktzoglou et al., Journal of Cardiovascular Magnetic Resonance, vol. 9 (2007) pp. 33-42.

"Flow-Dependent Arterial and Venous Imaging by Non-Contrast-enhanced Subtraction Angiography," Priest et al., Proc. ISMRM Toronto (2008) p. 727.

"Highly Accelerated Contrast-Enhanced MR Angiography Using Ghost Imaging," Edelman et al., Proc. Intl. Soc. Mag. Reson. Med., vol. 17 (2009), p. 272.

"Improvement in Delineation of Peripheral Arteries Using Non-Contrast-Enhanced 3D MRA with ECG-Triggered Half-Fourier FSE: Additional Spoiler Pulses in the Phase Encode Direction," Miyazaki et al., Proc. Intl. Soc. Mag. Reson. Med., vol. 11 (2004), p. 1945.

"$20^{th}$ Annual International Conference on Magnetic Resonance Angiography," Graz, Fan et al. (2008) pp. 1-131.

"Clinical Evaluation of Aortic Diseases Using Nonenhanced MRA with ECG-Triggered 3D Half-Fourier FSE," Urata et al., J. of Magnetic Resonance Imaging, vol. 14 (2001) pp. 113-120.

"A Novel Non-Contrast MR Angiography Technique Using Triggered Non-Selective Refocussed SPACE for Improved Spatial Resolution and Speed," Xu et al., Proc. Intl. Soc. Mag. Reson. Med., vol. 16 (2008), p. 730.

"NMR Angiography With Enhanced Quasi-Half-Echo Scanning," Guo, et al., Magnetic Resonance Imaging, vol. 9 (1991) pp. 129-139.

"MR Perfusion Studies with $T_1$-Weighted Echo Planar Imaging," Kwong, et al., Magnetic Resonance in Medicine, vol. 34 (1995) pp. 878-887.

* cited by examiner

MAGNETIC RESONANCE ANGIOGRAPHY WITH FLOW-COMPENSATED AND FLOW-SENSITIVE IMAGING

BACKGROUND OF THE INVENTION

1. Field of the Invention

The present invention concerns a method to generate an angiographic magnetic resonance image of an examination region and a magnetic resonance system for implementing such a method.

2. Description of the Prior Art

In magnetic resonance tomography there are multiple possibilities to show the blood vessels in angiograms that can either be based on a contrast agent-intensified signal acquisition, or acquired without contrast agent by using the effect of flowing magnetization during the image acquisition. Since not all examined persons tolerate the administration of contrast agent, magnetic resonance angiography that is not contrast agent-intensified is gaining importance.

In magnetic resonance angiography it is typically desirable to show only the arteries and to suppress the MR signal from the veins. In MR angiography that is not contrast agent-intensified, the method that is used depends on the desired examination region, i.e. on the blood flow conditions in this region. In peripheral body regions (for example the lower legs), the blood flow is typically slow. For MR angiography the pulsation of the arterial blood flow is used in order to generate MR angiograms that are not contrast agent-intensified. Typically an image acquisition technique is used in which blood delivers a high signal, i.e. a T2-weighted or T2/T1-weighted imaging frequency that is sensitive to flow. In such flow-sensitive imaging sequences, a quickly flowing magnetization delivers little signal; the vessels are dark. Such MR images with dark vessels are acquired in a data set in which the arterial flow is high, for example in the systoles of the cardiac cycle, which leads to an MR image with dark arteries, as desired.

Furthermore, an additional MR data set is acquired, for example in the diastoles during which the arteries ideally exhibit no flow or only a very slight flow, which leads to an MR image with bright arteries. By subtraction of the MR images that are acquired from the first and second data set, an MR angiography image is obtained that shows only the arteries. In the prior art it is known to use fast spin echo sequences for this purpose, for example, as is described in (among others) Miyazaki et al. in "Non-Contrast-Enhanced MR Angiography Using 3D ECG-Synchronized Half-Fourier Fast Spin Echo", Journal of Magnetic Resonance Imaging 12(5): 776-783, 2000. This angiography technique could be improved by, for example, flow spoiler gradients being added in the readout direction, so the flowing spins are additionally dephased, which additionally intensifies the signal obliteration in the arteries in the acquisition during the diastole (see Miyazaki et al. "Peripheral MR Angiography: Separation of Arteries from Veins with Flow-spoiled Gradient Pulses in Electrocardiography-triggered Three-dimensional Half-Fourier Fast Spin-Echo Imaging", Radiology 227(3): 890-896, 2003). It is likewise known to use gradient echo-based imaging sequences for such angiography methods, for example sequences known as TrueFISP sequences in which the transverse magnetization is refocused by gradient moments in all spatial directions. In such TrueFISP-based methods, the necessary flow sensitization is achieved by a dephasing preparation before every data acquisition in the systole, as is described in (among others) Koktzoglou et al. in "Diffusion-Prepared Segmented Steady-State Free Precession: Application to 3D Black-Blood Cardiovascular Magnetic Resonance of the Thoracic Aorta and Carotid Arterio Walls", Journal of Cardiovascular Magnetic Resonance 9(1): 33-42, 2007, and in Priest et al. in Proceedings ISMRM Toronto, Number 727, 2008. These methods, however, have the following disadvantage.

First, it has been shown in practice that it is very difficult for many patients to find a cardiac phase in which absolutely no flow occurs, such that the MR image with the bright flow signal often has regions with less signal or without signal in the arteries. This particularly applies for patients with rapid heart rates. Second, this type of angiography imaging is problematical, in particular in regions with fast flow. For example, with the aforementioned technique good results (i.e. good MR angiography images) can be achieved in the lower feet while it is more difficult to achieve the same result quality in the upper feet or the pelvis. The problem of signal obliterations in the arteries with high signal also occurs for patients with irregular heart beat since it is difficult to precisely determine the phase of the rapid flow during the systole and the phase of the low flow during the diastole.

In "Highly Accelerated Contrast-Enhanced MR Angiography using Ghost imaging" by R. R. Edelman et al. in Proc. Intl. Soc. Mag. Reson. Med. 17, S. 272, 2009, it is described that a mixed raw data set is generated instead of a subtraction of the signals in the two cardiac phases. In this method (in the simplest 3D execution variant) the even k-space lines (for example in the kz-direction, thus in the slice direction) are filled with data set 1 and the odd k-space lines are filled with data set 2; the transformation can thereby already be implemented or not in the readout direction and phase coding direction. A modulation of signal portions in which the two data sets differ is hereby generated in this direction. After transformation into image space in the kz-direction or z-direction (typically by Fourier transformation), a doubled 3D data set is obtained, so to speak, in which both a type of averaged original image and a second image exist, the second image being spatially separate (i.e. displaced in the z-direction as what is known as a "ghost image") and representing the differences of the two data sets. This new method for combination of two data sets is described as advantageous compared to a traditional subtraction, particularly given the use of high acceleration factors in parallel imaging.

A third disadvantage is that the strong pulsing of the vessels leads to changes in the vessel diameter, which can lead to false results in taking the difference of the images of the systole and the diastole. A fourth disadvantage of the method described above is that EKG triggering is necessary during the image acquisition in order to correlate the image acquisition with the heart beat for the acquisition of the MR images during the systole and the diastole.

In fast imaging sequences based on spin echo, the inherent flow sensitivity is greatest in the direction of the readout gradient. One possibility to reduce the large flow effects in the image acquisition is to select the phase coding gradients along the flow direction. However, in this case it is more difficult to achieve a sufficient flow sensitivity in the data set in which the vessels should be shown dark. Moreover, in most applications the phase coding direction runs in the head-foot direction. In such acquisitions the body of the examined person runs further outside of the imaged field of view (FOV) so that the problem can occur that signals from outside of the field of view are detected, or what is known as phase oversampling must be used in order to prevent aliasing artifacts.

SUMMARY OF THE INVENTION

An object of the present invention is to improve angiography that is not contrast agent-intensified and to increase the signal difference in the arteries given the acquisition of the two data sets in order to obtain high-contrast MR angiography images.

According to the invention, a method is provided to generate an MR angiography image in which a first MR data set of an examination region is acquired in which the vessels in the examination region are shown with high signal intensity. Furthermore, a second MR data set of the examination region is acquired in which the vessels in the examination region are shown with low signal intensity. An angiographic magnetic resonance image is calculated via mathematical combination of the first and second data set. According to the invention, the first data set is now acquired with an imaging sequence with reduced flow sensitivity and the second data set is acquired with an imaging sequence with a flow sensitivity increased relative to the first data set. According to the invention, the MR data set in which the vessels in the examination region are shown with high signal is thereby improved. In the acquisition of this first MR data set, the flow sensitivity is reduced, so an MR data set is generated that leads to an optimized bright signal in the arteries. The optimization of the first MR data set with light vessel depiction is of particular important area given fast blood flow or in patients with high or varying heart rate. The improvement of the bright signal portions in the vessels in the acquisition of the first MR data set leads to a higher stability of the angiography method. In particular, it is no longer necessary (as in the prior art) to detect the time period without flow in the arteries since the present method shows vessels with high signal even at low flow speeds. The problem of the signal obliteration in the first MR data set is therefore prevented. By the use of an essentially flow-insensitive imaging sequence and a flow-sensitive imaging sequence it is possible to show vessels with medium or fast flow speeds. The signal attenuation occurring in the center of the vessel (where the flow is highest) in conventional methods is avoided in the acquisition of the first data set. By the method according to the invention, this effect is avoided and the signal homogeneity in the vessels is improved in the first data set. An additional advantage of the method according to the invention is that the maximum speed and the minimum speed of the blood flow have a lesser importance to the acquisition of the two MR data sets than in previous methods. The image quality of the MR angiography image thus can be improved, even in the case of irregular heart rates in EKG-triggered acquisitions.

The first data set is advantageously acquired with an imaging sequence with a flow sensitivity that is reduced in comparison to a standard implementation of the sequence that is employed, while the second data set is acquired with an imaging sequence with a flow sensitivity that is normal or increased in comparison to the standard implementation. In the standard implementation, the flow sensitivity is the same in the acquisition of both data sets.

In one embodiment of the invention, the mathematical combination of the two data sets can be done by generating a single, temporarily inverse data set from the two data sets, the single, temporarily inverse data set being subsequently transformed through a suitable transformation into image space, as described in the Edelman article mentioned above. For example, in the case of a 3D angiography measurement the even kz lines in 3D raw data space (k-space) can be populated with data of the first data set and the odd kz lines can be populated with data of the second data set. This temporarily inverse data set exhibits a modulation of the signal intensity along the kz-direction, which leads to a ghost image of the arteries. For example, an image of the ghost image can be generated via the maximum intensity projection method and be rotated in three dimensions, as in a conventional method for the generation of an MR angiography exposure.

Another possibility is a simple subtraction of the two data sets to generate the MR angiography image.

The two MR data sets are advantageously synchronized to the cardiac cycle of an examination subject of whom the examination region is acquired.

The first MR data set is advantageously acquired during the diastole of the cardiac cycle in which the blood flow in the vessels in the examination region is slow, and the second MR data set is acquired during the systole of the cardiac cycle in which the blood flow in the vessels in the examination region is fast. However, if the imaging sequence with reduced flow sensitivity and the more flow-sensitive imaging sequence operate reliably, it is also possible to modify the data acquisition so that both the first data set and the second data set are acquired in the same cardiac phase, for example during the systole with fast arterial flow. In this embodiment the third disadvantage described above—that errors occur in the subtraction of the two MR images due to the pulsing state of the artery and the size difference during the systole and the diastole—can be prevented. If both data sets are acquired during the systole, the errors induced in the vessel disposition by pulsation can be reduced or, respectively, avoided in the vessel.

The imaging sequence for the acquisition of the first and second data set is advantageously identical except for the flow sensitivity. The reduced flow sensitivity of the first MR data set can be achieved in that the first gradient moment between successive RF pulses in the imaging sequence is reduced in comparison to the corresponding first gradient moment of the imaging sequence used to acquire the second MR data set, at least for the primary flow direction. The different flow sensitivity is hereby achieved in the acquisition of the first and second data set. For example, the first gradient moment between successive RF pulses in the imaging sequence used to acquire the first MR data set can be less by at least a factor of two than the first gradient moment of the imaging sequence that is used to acquire the second data set, wherein this applies at least for the primary flow direction. In another embodiment it is possible to achieve the reduced flow sensitivity of the first MR data set in that the first gradient moment is nulled (zeroed) (or at least subsequently nulled) between successive RF pulses in the imaging sequence, at least for the primary flow direction. Given such a flow-compensated gradient switching, the effect of flowing spins on the MR signal is minimized. Another possibility for the flow compensation or the reduction of the flow sensitivity is to achieve the first data set with the aid of a predetermined workflow scheme in the acquisition of k-space. For example, predetermined schemes (known as reordering schemes) can be used, as is described for fast spin echo sequences in (for example) Hinks et al., "Gradient Moment Nulling in Fast Spin Echo", Magnetic Resonance in Medicine 32(6): 698-706, 1994, or for TrueFISP sequences in Bieri et al. in "Flow Compensation in Balanced SSFP Sequences", Magnetic Resonance in Medicine 54(4): 901-907, 2005.

In the combination of an imaging sequence with reduced and increased flow sensitivity to acquire the first or, respectively, second data set, the signal of the vessels is repeatedly determined via the design of the imaging sequence that is used, and no longer via the cardiac phase. Based on this fact it is also possible to no longer implement the acquisition of the first and second data set in an EKG-triggered manner.

The increased flow sensitivity of the second MR data set can also be achieved by activating a flow-dephased preparation before the actual imaging sequence, or before sub-segments of the actual imaging sequence. It is likewise possible to acquire one of the two data sets using a series of RF pulses with variable flip angles, with the difference of the flow sensitivities of the first MR data set and of the second MR data set being achieved or additionally emphasized by the use of different flip angle curves.

The two data sets are advantageously acquired in temporally interleaved sub-segments.

The invention furthermore concerns a magnetic resonance system to generate the angiographic MR image, having an imaging control unit that controls the acquisition of the first and second data set as described above. Furthermore, an image computer is provided that calculates the angiographic MR image by difference calculation. The imaging sequence control unit controls the acquisition of the first and second data set with reduced or, respectively, increased flow sensitivity as described above.

DESCRIPTION OF THE PREFERRED EMBODIMENTS

Figure 1:
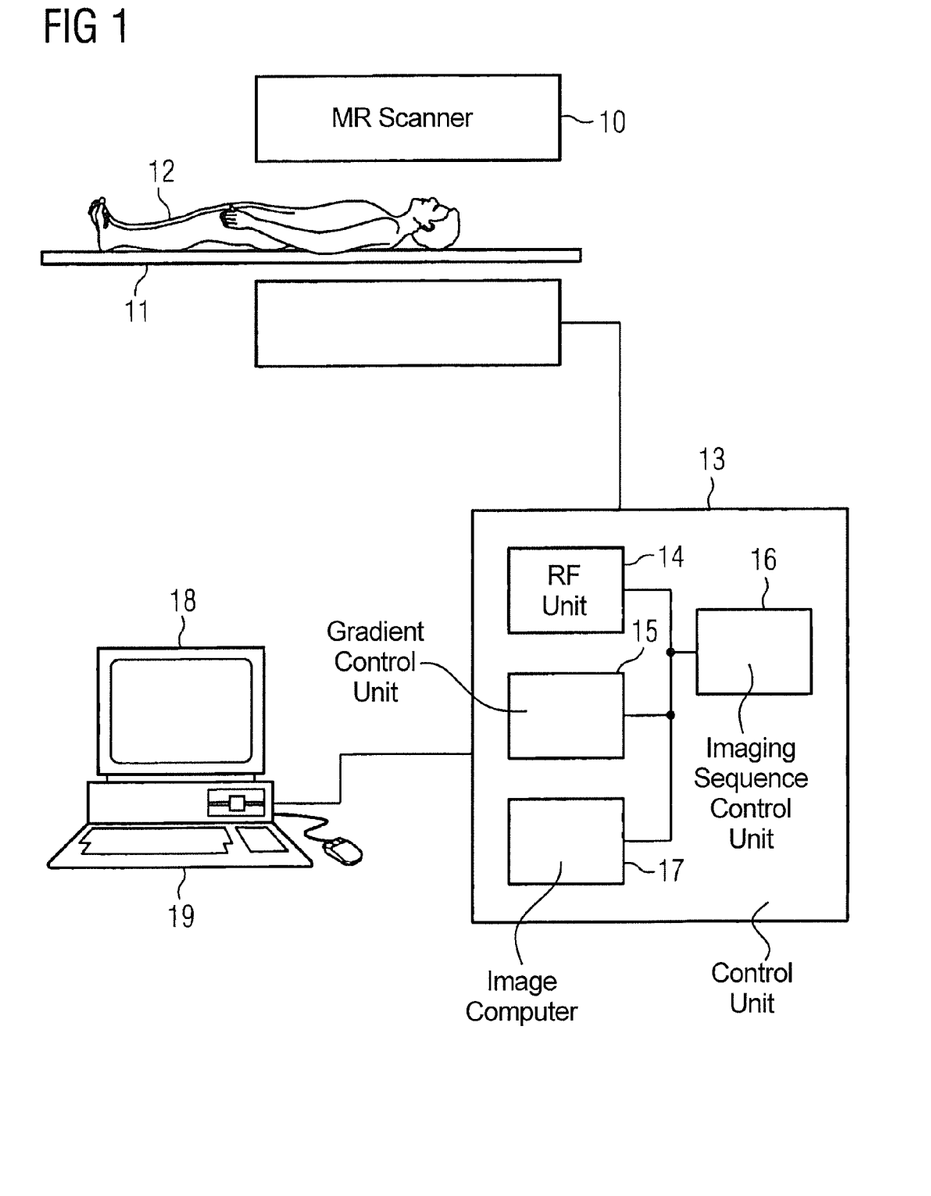
FIG. 1 schematically illustrates an MR system to generate the angiographic MR image.

Shown in FIG. 1 is an MR system with which MR angiography images according to the invention can be generated with which a better image quality is achieved via improvement of the MR acquisition with bright vessel depiction. The MR system has scanner 10 that contains a basic field magnet to generate a polarization field B0. An examination subject 12 arranged on a bed 11 is driven into the middle of the magnet where the acquisition of the MR signals from an examination region is implemented by radiation of RF pulses and switching (activation/deactivation) of gradients in the scanner 10. The manner by which MR images can be generated in a pulse sequence with a progression of RF pulses and switching of gradients is known to those skilled in the art and need not be described in detail herein. The MR system is connected with a central control unit 13 with which the MR system is controlled. The central control unit moreover has an RF control unit 14 that controls the switching of the RF pulses to deflect the magnetization. A gradient control unit 15 controls the switching of the magnetic field gradients for spatial coding of the excited spins. An imaging sequence control unit 16 controls the workflow of the gradient switching, the RF pulses and the signal readout depending on the selected imaging sequence. From the MR signals detected with a coil (not shown) an MR image computer 17 calculates MR images by Fourier transformation (as is known) that can be displayed on a display unit 18. The MR system can be controlled by an operator at an operating unit 19. The other typical components of an MR system have been omitted for clarity.

Figure 2:
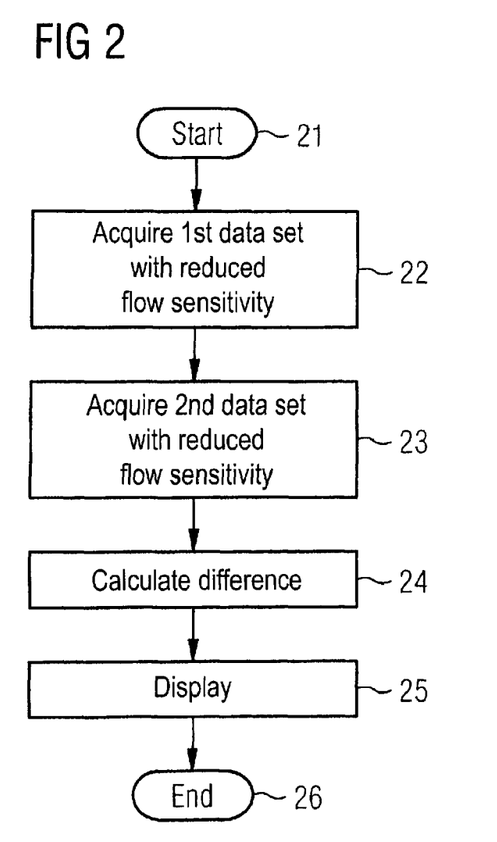
FIG. 2 is a flowchart with steps to generate the angiographic MR image.

In FIG. 2 a flowchart is shown that includes the steps that lead to the improvement of the MR angiography in regions with fast blood flow or patients with high heart rates. The method starts in Step 21, wherein in Step 22 the first MR data set is acquired with a flow-insensitive imaging sequence or an imaging sequence with reduced flow sensitivity. Given the use of a flow-sensitive imaging sequence, fast-flowing spins would lead to signal obliteration due to the dephasing of the spins along the gradient, such that the arteries would be shown dark. For example, this can be prevented via a flow-compensated gradient switching in which the spins with constant speed are not dephased via switching of additional gradients or via specific acquisition schemes of k-space. A fast spin echo sequence (turbo spin echo) or, for example, a TrueFISP sequence—also known as a balanced SSFP (Steady State Free Precession) sequence—can be used as an imaging sequence. This first data set can be acquired during the diastole; however, it is also possible to implement the acquisition without EKG triggering. In Step 23, the second data set is acquired with an imaging sequence with an increased flow sensitivity relative to the first data set. If the first data set is acquired with a fast spin echo sequence (TSE), the second data set is likewise acquired with a fast spin echo sequence, and in the case of a TrueFISP sequence in acquisition of the first data set a TrueFISP sequence is likewise used in acquisition of the second data set. The flow sensitivity or the different degrees of brightness in the vessels can also be achieved via different imaging parameters, for example different echo times in the fast spin echo sequence. The second data set can be acquired during the diastole. However, it is likewise possible to similarly acquire the second data set in the systole of the cardiac cycle in order to reduce the influence of the pulsation of the vessels in the acquisition of the two data sets. An acquisition without EKG triggering is likewise possible if the first data set was also acquired without EKG triggering. It is naturally also possible to acquire the second data set and then the first data set.

The following table gives an overview of possible different implementations to acquire the two data sets.

| Sequence | 2nd data set | 1st data set | |
|---|---|---|---|
| TSE | Systole | Diastole | flow-compensated |
| TSE | Systole | Systole | flow-compensated |
| TSE | Without EKG | Without EKG | flow-compensated |
| TrueFISP | Systole | Diastole | flow-compensated |
| TrueFISP | Systole | Systole | flow-compensated |
| TrueFISP | Without EKG | Without EKG | flow-compensated |

In Step 24 the flow-sensitive data can then be subtracted from the flow-compensated data, whereby only the light signals remain in the arteries. The calculation of angiography images from a series of 2D data sets or 3D data sets is known to those skilled in the art and thus need not be described in detail herein. Finally, the angiography image or the angiography images can be displayed in Step 25 before the method ends in Step 26. The flow compensation and flow sensitization can each ensue only in the primary flow direction, i.e. in one direction, but it is also possible to apply the flow compensation and flow sensitization in two or three spatial directions, for example if the depicted vessel exhibits components not only in one spatial direction. In particular, given branchings of vessels the flow compensation and flow sensitization can bring improvements in multiple spatial direction.

Figure 3:
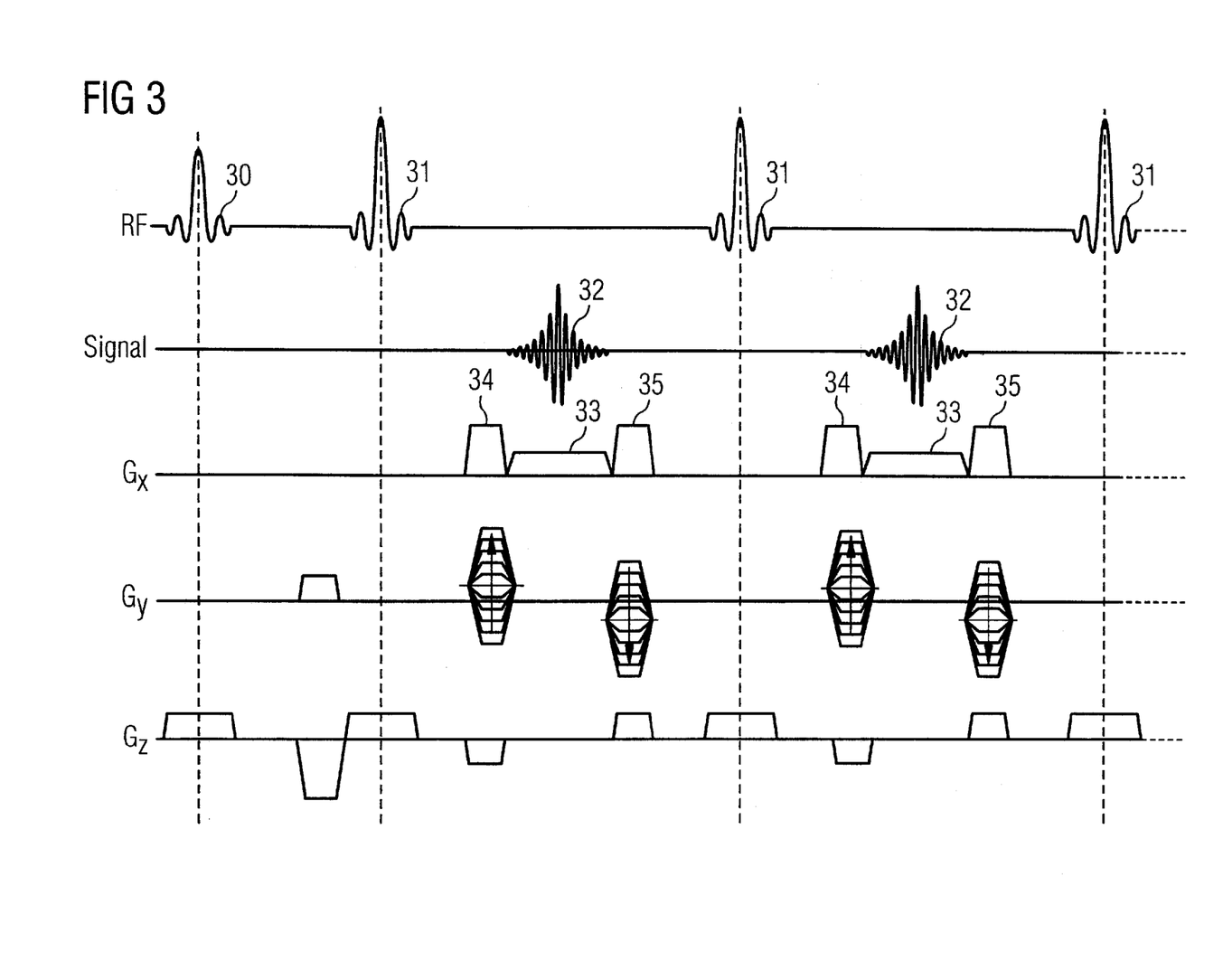
FIG. 3 shows a flow-sensitive fast spin echo sequence that can be used to generate the second data set.
Figure 4:
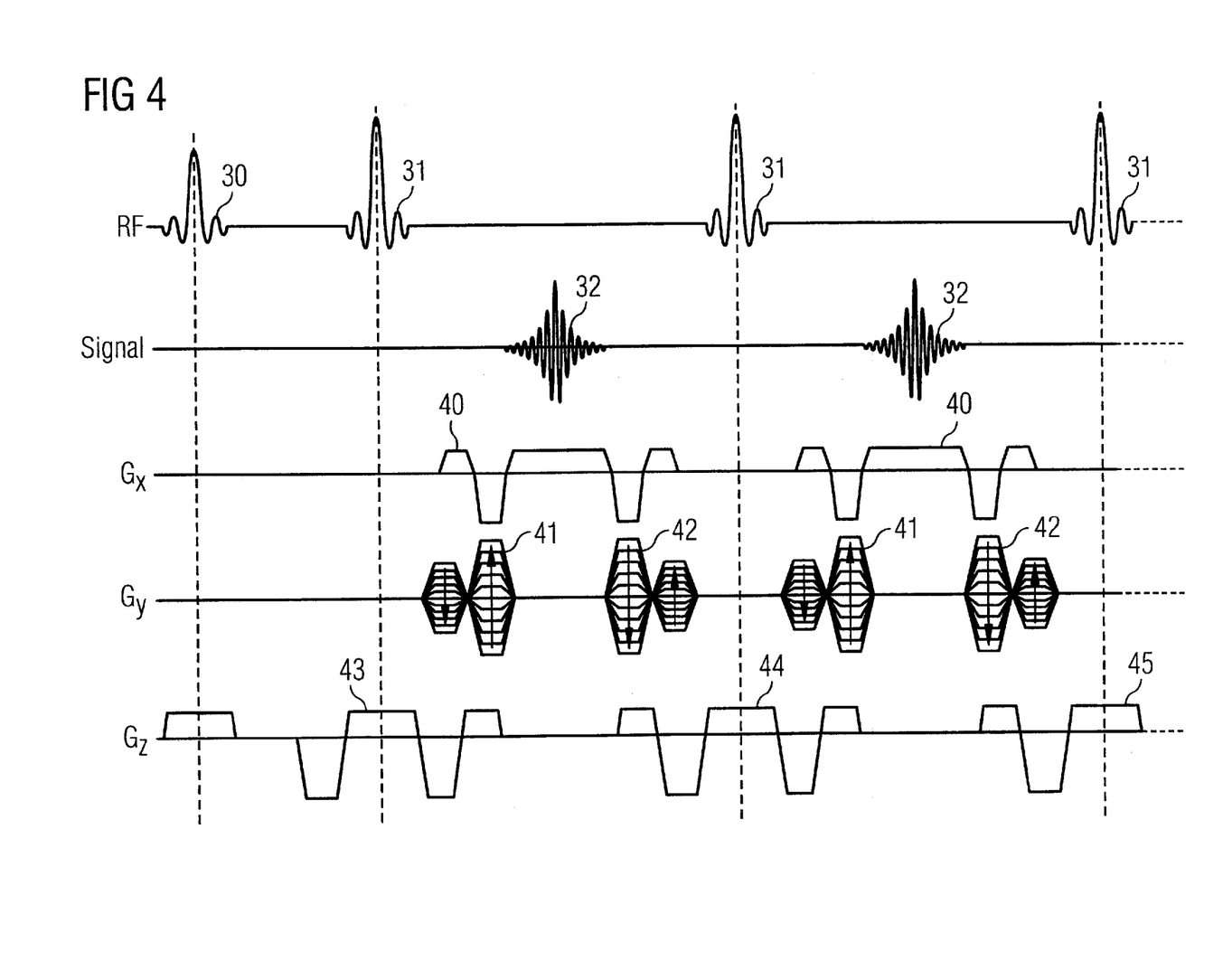
FIG. 4 shows a flow-compensated fast spin echo sequence that can be used to generate the first data set.

In FIG. 3 a scheme of a fast 2D spin echo sequence with increased flow sensitivity in the $G_x$ direction is shown. As is known, the 180° refocusing pulses 31 follow after a 90° RF pulse 30, whereby the spin echoes 32 are generated. The gradient switching ensues in the phase coding direction $G_y$ and slice selection direction $G_z$, as is typically known in a fast spin echo imaging sequence. In addition to the readout gradient 33, additional gradients 34 and 35 are switched in the readout direction $G_x$ during the signal acquisition in order to achieve an additional dephasing of the flowing spins in the blood vessel. This imaging sequence shown in FIG. 3 can be used, for example, to obtain the second data set. A fast, flow-compensated spin echo sequence with the sequence of the 90° pulse 30 and the 180° pulses with which the first data set can be acquired is shown in FIG. 4. Among other things the imaging sequence drawn here deals with achieving what is known as the first magnetic moment M1 via a determined segment of the imaging sequence. This first moment M1 corresponds to the temporal integral over the product of the gradient magnitude G·t and is a criterion for which phase also receives a magnetization with different speeds. For example, given a flow-compensated imaging sequence this is zero at the signal readout, which however costs additional time and would lead to larger intervals between two the echoes. For this reason the magnetic moment M1 in the example shown in FIG. 4 is zero where the RF pulses are radiated. This is achieved in the readout direction via the gradient switching 40, by the gradient switching 41 and 42 in the phase coding direction and by the gradient switchings 43, 44 and 45 in the slice-selection direction. The gradient switchings 40 through 45 are now switched so that the product gradient G·t is zero where RF pulses are radiated.

Figure 5:
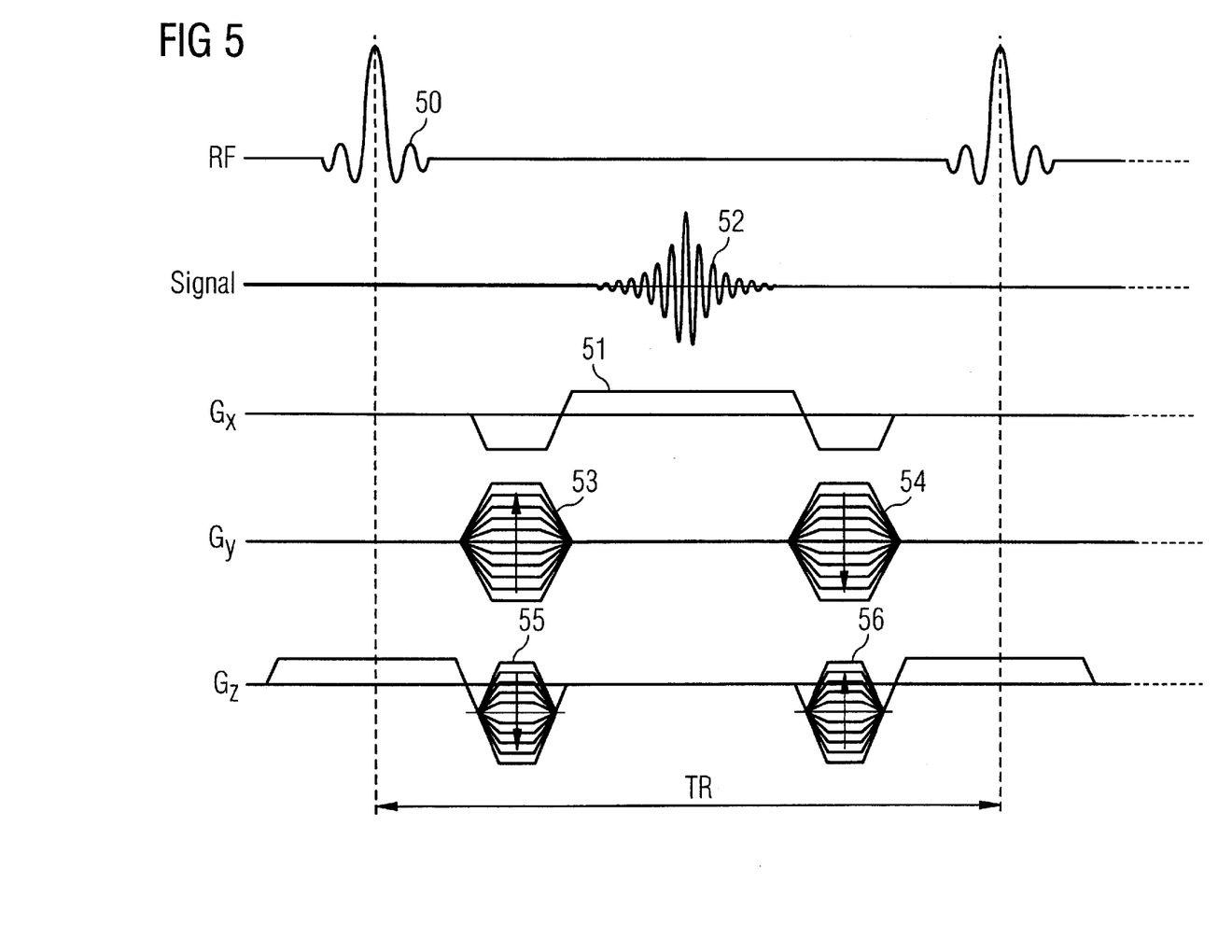
FIG. 5 shows a flow-sensitive TrueFISP sequence to generate the second data set with the aid of gradient echo-based signals.
Figure 6:
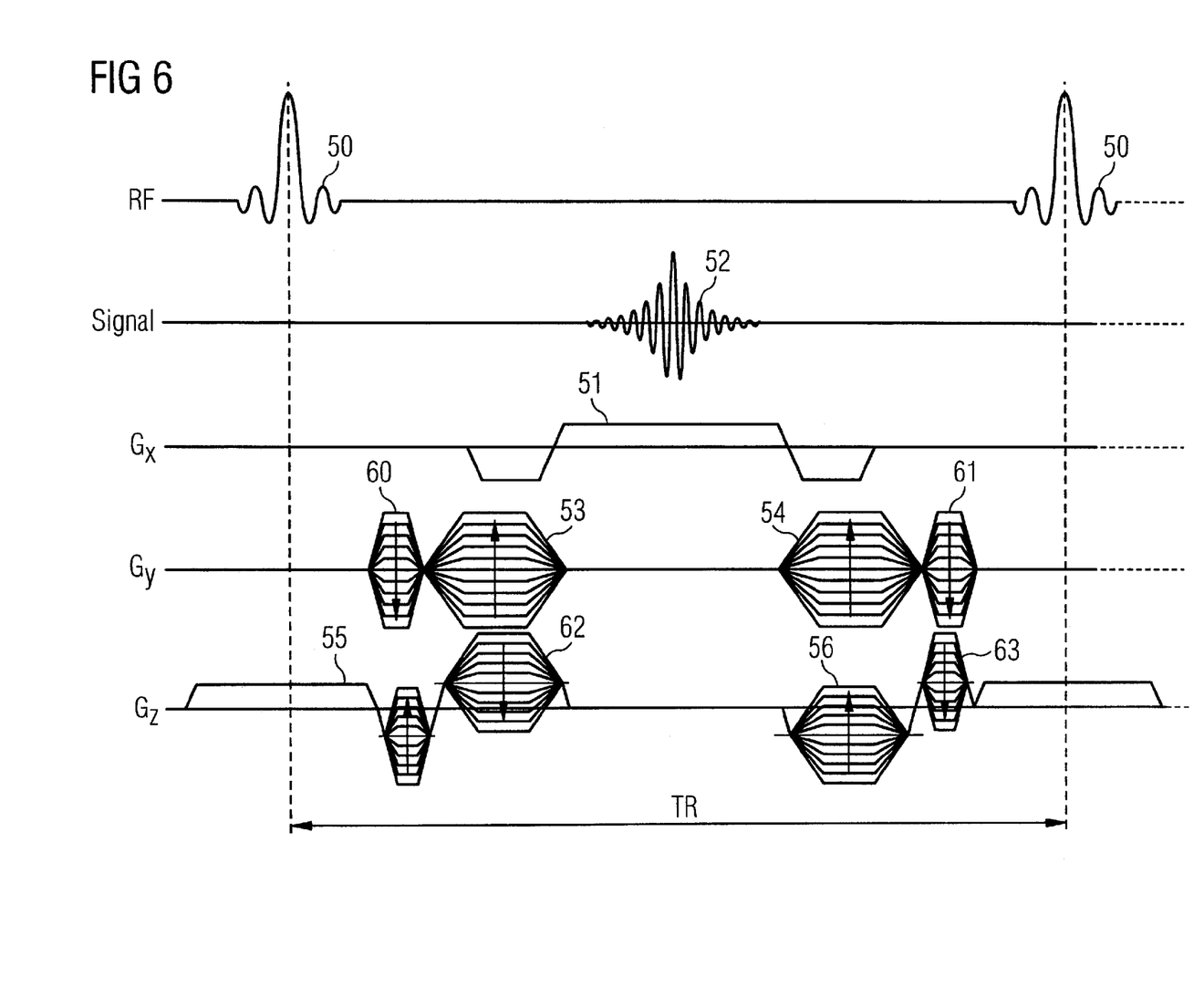
FIG. 6 shows a flow-compensated TrueFISP sequence to generate the first data set with the aid of gradient echo.

A three-dimensional TrueFISP sequence that is flow-sensitive and with which the second data set can be acquired is shown by way of example in FIG. 5. After radiation of an RF pulse 50, the gradient switching 51 ensues in the readout direction $G_x$, whereby the echo 52 is generated. The gradient switchings in the phase coding direction 53 and 54 as well as in the slice-selection direction 55 and 56 are thereby switched so that the magnetic moments are returned to zero in all three spatial directions. In FIG. 6 the TrueFISP sequence of FIG. 5 is shown with flow compensation. The flow compensation in the phase coding direction is achieved via switching of additional gradients with the gradient switching 60 and 61 and in the slice-selection direction by the additional switchings 62 and 63.

In the examples shown in FIGS. 3 through 6, the flow sensitization and flow compensation have been achieved via switching of gradients. However, it is likewise possible to modify the order of the acquisition of the k-space points in order to acquire data sets with larger and smaller flow sensitivity or to switch preparation modules before the acquisition or before sub-segments of the acquisition, for example by activating a 90° pulse and a −90° pulse in order to achieve a dephasing of all moving spins, which leads to an increased flow sensitivity of a sequence.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate a magnetic resonance angiography image of an examination region of a subject, comprising the steps of:
    operating a magnetic resonance data acquisition unit in which an examination subject is located according to an imaging sequence with reduced flow sensitivity to acquire a first magnetic resonance dataset from an examination region of the subject in which vessels in the examination region are shown with high signal intensity;
    operating said magnetic resonance data acquisition unit according to an imaging sequence with a flow sensitivity that is increased compared to the reduced flow sensitivity with which the first magnetic resonance data set was acquired, to obtain a second set of magnetic resonance data from the examination region in which the vessels in the examination region are shown with a low signal intensity;
    synchronizing acquisition of each of said first and second magnetic resonance data sets with a cardiac cycle of the examination subject;
    acquiring all of said first magnetic resonance data set during a diastole of said cardiac cycle, in which blood flow in the vessels in the examination region is slow, and acquiring all of said second magnetic resonance data set during systole of said cardiac cycle, in which blood flow in the vessels in the examination region is faster compared to blood flow during acquisition of said first magnetic resonance data set; and
    in a processor, reconstructing an angiographic magnetic resonance image of the examination region by mathematically combining said first and second magnetic resonance data sets.

2. A method as claimed in claim 1 comprising mathematically combining said first and second magnetic resonance data sets by generating a single, temporarily inverse data set from said first and second magnetic resonance data sets and transforming said single, temporarily inverse data set into image space.

3. A method as claimed in claim 1 comprising mathematically combining said first and second magnetic resonance data sets by subtracting one of said first and second magnetic resonance data sets from the other of said first and second magnetic resonance data sets.

4. A method as claimed in claim 1 comprising acquiring said first and second magnetic resonance data sets respectively with an imaging sequence that is identical except for said flow sensitivity.

5. A method as claimed in claim 4 comprising employing, as said same imaging sequence for acquiring each of said first and second magnetic resonance data sets, an imaging sequence having a gradient field exhibiting a gradient moment that is activated between successively radiated RF pulses, and reducing the flow sensitivity during acquisition of said first magnetic resonance data set by reducing said gradient moment, at least in a primary direction of said flow, when acquiring said first magnetic resonance data set compared to when acquiring said second magnetic resonance data set.

6. A method as claimed in claim 5 comprising reducing said gradient moment by at least a factor of two.

7. A method as claimed in claim 5 comprising reducing said gradient moment by substantially nulling said gradient moment, at least in said primary flow direction, during acquisition of said first magnetic resonance data set.

8. A method as claimed in claim 1 comprising reducing said flow sensitivity during acquisition of said first magnetic resonance data set by using a predetermined procedure for entering data into k-space.

9. A method as claimed in claim 1 comprising producing the increased flow sensitivity during acquisition of said second magnetic resonance data set by activating at least one spoiler gradient in said imaging sequence.

10. A method as claimed in claim 1 comprising producing said increased flow sensitivity during acquisition of said second magnetic resonance data set by activating a flow-dephased preparation before at least a portion of said imaging sequence.

11. A method as claimed in claim 1 comprising acquiring at least one of said first and second magnetic resonance data sets by radiating a series of RF pulses in said imaging sequence having respectively different flip angles, and producing different flow sensitivities during acquisition of said first and second magnetic resonance data sets using different curves for said flip angles.

12. A method as claimed in claim 1 comprising selecting said imaging sequence from the group consisting of turbo spin echo imaging sequences and balanced SSFP imaging sequences.

13. A method as claimed in claim 1 comprising acquiring said first and second magnetic resonance data sets in temporally interleaved sub-segments.

14. A magnetic resonance apparatus that generates a magnetic resonance angiography image of an examination region of a subject, comprising:

a magnetic resonance data acquisition unit adapted to receive an examination subject therein;

a control unit configured to operate said data acquisition unit according to an imaging sequence with reduced flow sensitivity to acquire a first magnetic resonance dataset from an examination region of the subject in which vessels in the examination region are shown with high signal intensity;

said control unit also being configured to operate said magnetic resonance data acquisition unit according to an imaging sequence with a flow sensitivity that is increased compared to the reduced flow sensitivity with which the first magnetic resonance data set was acquired, to obtain a second set of magnetic resonance data from the examination region in which the vessels in the examination region are shown with a low signal intensity;

said control unit being configured to operate said data acquisition unit to acquire each of said first and second magnetic resonance data sets synchronized with a cardiac cycle of the examination subject, with all of said first magnetic resonance data set being acquired during a diastolic phase of a cardiac cycle, in which blood flow in the vessels in the examination region is slow, and with all of said second magnetic resonance data set being acquired during a systolic phase of said cardiac cycle, in which blood flow in the vessels in the examination region is faster compared to blood flow during acquisition of said first magnetic resonance data set; and a processor configured to reconstruct an angiographic magnetic resonance image of the examination region by mathematically combining said first and second magnetic resonance data sets.

* * * * *